United States Patent [19]

Toole, Jr. et al.

[11] Patent Number: 4,757,006

[45] Date of Patent: Jul. 12, 1988

[54] HUMAN FACTOR VIII:C GENE AND RECOMBINANT METHODS FOR PRODUCTION

[75] Inventors: John J. Toole, Jr., Brookline; Edward Fritsch, Concord, both of Mass.

[73] Assignee: Genetics Institute, Inc., Cambridge, Mass.

[21] Appl. No.: 546,650

[22] Filed: Oct. 28, 1983

[51] Int. Cl.$^4$ .................. C12P 21/02; C12Q 1/68; C12N 15/00; C12N 5/00; C12N 1/00; C07H 15/12

[52] U.S. Cl. .................................. 435/70; 435/6; 435/172.3; 435/240.2; 435/320; 536/27; 935/9; 935/11; 935/78

[58] Field of Search ................ 435/68, 70, 172.3, 317, 435/6, 320, 240.2; 536/27; 935/9, 11, 78

[56] References Cited

U.S. PATENT DOCUMENTS

| | | | |
|---|---|---|---|
| 4,332,893 | 6/1982 | Rosenberg | 435/240 |
| 4,363,877 | 12/1982 | Goodman et al. | 435/317 |
| 4,399,216 | 8/1983 | Axel et al. | 435/6 |
| 4,419,446 | 12/1983 | Howley et al. | 435/172.3 |

OTHER PUBLICATIONS

Montgomery et al., Cell, vol. 14, pp. 673–680, Jul. 1978.
Kunnaird et al., Gene, vol. 20, pp. 387–396, 1982.
Woods et al., PNAS U.S.A., vol. 79, pp. 5661–5665, Sep. 1982.
Lawn et al., Cell, vol. 15, pp. 1157–1174, Dec. 1978.
Tashima et al., PNAS U.S.A., vol. 78, pp. 1508–1512, Mar. 1981.
Ullrich et al., Science, vol. 209, pp. 612–615, Aug. 1, 1980.
Thummel et al., Eukaryolic Viral Vectors, Ed. by Gluzman, Cold Spring Harb. Lab., pp. 181–186, (1982).
Suggs et al., PNAS U.S.A., vol. 78, pp. 6613–6617, Nov. 1981.
Choo et al., Nature, vol. 299, pp. 178–180, Sep. 9, 1982.
Kurachi et al., PNAS U.S.A., vol. 79, pp. 6461–6464, Nov. 1982.
Tuddenham et al., The J. Lab. Clin. Med., vol. 93, No. 1, pp. 40–53, Jan. 1979.
Fulcher et al., PNAS U.S.A., vol. 79, pp. 1648–1652, Mar. 1982.
Fay et al., PNAS U.S.A., vol. 79, pp. 7200–7204, Dec. 1982.
Kuo et al., Poster Presentation, 9th International Congress on Thrombosis and Hemostasis, Jul. 4–8, 1983.
Wallace et al., Nucleii Acids Research, vol. 9, No. 4, pp. 879–894, (1981).
Mevarch et al., The J. of Biol. Chem., vol. 254, No. 16, pp. 7472–7475, Aug. 25, 1979.
J. D. Watson, Molecular Biology of the Gene, 347–77, (1977).
David Fass et al., "Blood", 59:594–600, (1982).
Knutsen et al., "Blood", 59:615–24, (1982).
Sinensky, "Biochem. Biophys. Res. Commun.", 78:863, (1977).
Meuth et al., "Cell", 3:367, (1943).
Kempe et al., "Cell", 9:541, (1976).
DeBatisse et al., "Mol. and Cell Biol.", 2(11):1346–1353, (1982).
Mulligan et al., "Proc. Nat. Acad. Sci.", 78[4]:2072–2076, (1981).
Colbere-Garapin et al., "J. Mol. Biol.", 150:1–14, (1981).
Harber et al., "Somatic Cell Genet.", 4:499–508, (1982).
Wigler et al., "Cell", 16:777–785, (1979).
Rigby et al., "J. Mol. Biol.", 113:237, (1977).
Laemmli, "Nature", 227–680, (1970).
L. Letsinger, et al., "J. Am. Chem. Soc.", 98:3655, (1976).
Matteucci and Caruthers, "J. Am. Soc.", 103:3185, (1981).

(List continued on next page.)

*Primary Examiner*—Alvin E. Tanenholtz
*Attorney, Agent, or Firm*—Sewall P. Bronstein; David G. Conlin; Gregory D. Williams

[57] ABSTRACT

The protein having factor VIII:C procoagulant activity has been produced by culturing a cell transformed with a recombinant expression vector encoding the gene for that activity.

8 Claims, 6 Drawing Sheets

A. Amino Acid Sequence of 69 Kd Porcine AKF Fragment

| Phe | Gln | Lys | Arg | Thr | Arg | His | Tyr | Phe |
|---|---|---|---|---|---|---|---|---|
| Ile | Ala | Ala | Val | Glu | Gln | Leu | Trp | Asp |
| Tyr | Gly | Met | Ser | Glu | Ser | Pro | Arg | Ala |
| Leu | Arg | Asn | Arg | Ala | Gln | Asn | Gly | Glu |
| Val | Pro | Arg | Phe | Lys | | | | |

B. Amino Acid Sequence Encoded by Porcine AHF Exon (34-H1)

| Arg | Ser | Phe | Gln | Lys | Arg | Thr | Arg | His | Tyr | Phe |
|---|---|---|---|---|---|---|---|---|---|---|
| | | Ile | Ala | Ala | Val | Glu | Gln | Leu | Trp | Asp |
| | | Tyr | Gly | Met | Ser | Glu | Ser | Pro | Arg | Ala |

C. Amino Acid Sequence Encoded in Human AHF Exon (25-S1)

| Arg | Ser | Phe | Gln | Lys | Lys | Thr | Arg | His | Tyr |
|---|---|---|---|---|---|---|---|---|---|
| | Phe | Ile | Ala | Ala | Val | Glu | Arg | | |

OTHER PUBLICATIONS

H. Fritz et al., "Biochemistry", 17:1257, (1978).
Sanger et al., "PNAS U.S.A.", 70:1209, (1973).
Maxam-Gilbert, "Meth. Enzymology", 65:499, (1980).
M. Jaye et al., "Nucleic Acids Research", 11:2325, (1983).
K. L. Agarwal et al., "J. Biol. Chem.", 256:1023, (1981).
Loenen et al., "Gene", 20:249, (1980).
Piccini et al., "Cell", 30:205, (1982).
Sanger et al., "PNAS U.S.A.", 74:5463, (1977).
Maniatis et al., "Cell", 15:687, (1978).
Cox, "Methods Enzymol.", 12B:120, (1968).
Ullrich et al., "Nature", 303:821, (1983).
Grunstein and Hogness, "PNSA U.S.A.", 72:3961, (1975).
Holmes et al., "Anal. Biochem.", 114:193, (1981).
E. Southern "J. Mol. Biol.", 98:503, (1975).
Benton et al., "Science", 196:180, (1977).

FIGURE 1

A. Amino Acid Sequence of 69 Kd Porcine AKF Fragment

| | | | | | | | | |
|---|---|---|---|---|---|---|---|---|
| | Phe | Gln | Lys | Arg | Thr | Arg | His | Tyr | Phe |
| | Ile | Ala | Ala | Val | Glu | Gln | Leu | Trp | Asp |
| | Tyr | Gly | Met | Ser | Glu | Ser | Pro | Arg | Ala |
| | Leu | Arg | Asn | Arg | Ala | Gln | Asn | Gly | Glu |
| | Val | Pro | Arg | Phe | Lys | | | | |

B. Amino Acid Sequence Encoded by Porcine AHF Exon (34-H1)

| | | | | | | | | |
|---|---|---|---|---|---|---|---|---|
| Arg | Ser | Phe | Gln | Lys | Arg | Thr | Arg | His | Tyr | Phe |
| | | Ile | Ala | Ala | Val | Glu | Gln | Leu | Trp | Asp |
| | | Tyr | Gly | Met | Ser | Glu | Ser | Pro | Arg | Ala |

C. Amino Acid Sequence Encoded in Human AHF Exon (25-S1)

| | | | | | | | | |
|---|---|---|---|---|---|---|---|---|
| Arg | Ser | Phe | Gln | Lys | Lys | Thr | Arg | His | Tyr |
| | Phe | Ile | Ala | Ala | Val | Glu | Arg | | |

FIGURE 2

A. Amines Terminus of 166Kd Polypeptide

X I R R Y Y L G A V E L S W D Y R Q S E L L R E L H V D T R F P A

B. Fragment of 166Kd Polypeptide

| Amino Acid No. | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|
| Amino Acid Sequence | His | Tyr | Phe | Ile | Ala | Ala | Val | Glu | Gln | Leu | Trp | Asp | Try | Gly | Met |
| Possible mRNA Sequences | CAU CAC | UAU UAC | UUU UUC | AUU AUC AUA | GCU GCC GCA GCG | GCU GCC GCA GCG | GUU GUC GUA GUG | GAA GAG | CAA CAG | CUU CUC CUA CUG UUA UUG | UGG | GAU GAC | UAU UAC | GCU GGC GGA GBG | ALG |
| Guessed Probe Sequence | GTG | ATG | AAA AAG | TAA | CGA | CGA | CAC | CTT CTC | GTC | GAC | ACC | CTA CTG | ATA | CCG | TAC |
| Actual Probe Sequence | GTG | ATA | AAG | TAA | CGA | CGC | CAC | CTC | GTC | GAG | ACC | CTA | ATG | CCC | TAC |

FIGURE 4

| | | | | | | | | |
|---|---|---|---|---|---|---|---|---|
| AAA | ACA | CGG | GGC | ACC | TGT | TAA | CCT | 27 GAA |
| CAA | AGT | AAA | TAG | ACC | TGG | AAG | GAC | 54 TCC |
| CTC | CAA | GCT | TCT | GGG | TCC | CCC | GAT | 81 GCC |
| CAA | AGA | GTG | GGA | ATC | CCT | AGA | GAA | 108 GTC |
| ACC | AAA | AAG | CAA | AGC | TCT | CAG | GAC | 135 GAA |
| AGA | CAT | CAT | CAG | TTT | ACC | CCT | GGA | 162 CCG |
| TCA | CGA | AAG | CAA | TCA | TTC | AAT | AGC | 189 AGC |
| AAA | AAA | TGA | AGG | ACA | AGC | CGA | GAC | 216 CCA |
| AAG | AGA | AGC | CGC | CTG | GAC | GAA | GCA | 243 GGG |
| AGG | GCC | TGG | AAG | GCT | GTG | CGC | TCC | 270 AAA |
| GCC | TCC | GGT | CCT | GCG | ACG | GCA | TCA | 297 GAG |
| GGA | CAT | AAG | CCT | TCC | TAC | TTT | TJA* | 324 CCC |
| GGA | GGA | AGA | CAA | AAT | GGA | CTA | TGA | 351 TGA |
| TAT | CTT | CTA | ACT | GAA | ACG | AAG | GGA | 378 GAA |
| GAT | TTT | GAC | ATT | TAC | GGT | GAG | GAT | 405 GAA |
| AAT | CAG | GAC | CCT | CGC | AGC | TTT | CAG | 432 AAG |
| AGA | ACC | CGA | CAC | TAT | TTC | ATT | GCT | 459 GCG |
| GTG | GAG | CAG | CTC | TGG | GAT | TAC | GGG | 486 ATG |
| AGC | GAA | TCC | CCC | CGG | GCG | CTA | AGA | 513 AAC |
| AGG | TAT | GGC | TAC | GTT | GGC | TAC | TCC | 540 TCT |
| GTC | CTA | CCC | TGG | GGA | CCT | TTG | TCT | 567 TGA |
| GCA | GGT | GCC | GAA | GCC | ATG | GGA | AAG | 594 GCA |
| CAA | GCA | GTC | TGG | GGG | TGG | AGA | GGC | 621 CAC |
| AGT | GGG | AGG | ATG | TGC | TTG | TTG | GGG | 648 AGC |
| ACA | GCG | TGG | TCG | GGC | AGG | GAA | GAG | 675 CAG |
| ACC | GAC | CTG | AGG | AGA | G | | | |

\* J Indicates an ambiguity, in accordance with the Stanford code.

FIGURE 5

```
     (250)              9                    18                   27
 5'   TGG  AAG   GCT   GTG   CGC   TCC   AAA   GCC   TCC   GGT   CCT 36           45                                      63
      GCG  ACG   GCA   TCA   GAG   GGA   CAT   AAG   CCT   TCC   TAC 72           81                  90                  99
      TTT  TJA   CCC   GGA   GGA   AGA   CAA   AAT   GGA   CTA   TGA 108           117                126
      TGA  TAT   CTT   CTA   ACT   GAA   ACG   AAG   GGA   GAA   GAT 135          144          153                162
      TTT  GAC   ATT   TAC   GGT   GAG   GAT   GAA   AAT   CAG   GAC 171          180                189                 198
      CCT  CGC   AGC   TTT   CAG   AAG   AGA   ACC   CGA   CAC   TAT
            R     S     F     Q     K     R     T     R     H     Y 207          216                225
      TTC  ATT   GCT   GCG   GTG   GAG   CAG   CTC  [TGG   GAT   TAC
       F    I     A     A     V     E     Q     L     W     D     Y 234          243          252                261
      GGG  ATG]  AGC   GAA   TCC   CCC   CGG   GCG   CTA   AGA
       G    M     S     E     S     P     R     A     L     R

267
      AAC  AGG   TAT   GGC   TAC   GTT   GGC   TAC   TCC   TCT
       N    R

GTC  CTA   CCC   TGG   GGA   CCT   TTG   TCT   TGA   GCA

GGT  GCC   GAA   GCC   ATG   GGA   AAG   GCA   CAA   GCA

GTC  TGG   GGG   TGG   AGA   (3')
```

FIGURE 6

HUMAN SEQ. DATA    (Complement of 15 mer desired sequence)

5'   GAC   ATT   TAT   GAT   GAG   GAT   GAA

ATT   CAG   AGC   CCC   CGC   AGC   TTT

CAG   AAG   AAA   ACA   CGA   CAC   TAT

TTT   ATT   GCT   GCA   GTG   GAG   AGG

HUMAN FACTOR VIII:C GENE AND RECOMBINANT METHODS FOR PRODUCTION

BACKGROUND OF THE INVENTION

This invention relates to the preparation of recombinant DNA which codes for cellular production of human factor VIII:C, and of DNA which codes for porcine factor VIII:C, to methods of obtaining DNA molecules which code for factor VIII:C, and to expression of human and porcine factor VIII:C utilizing such DNA, as well as to novel compounds, including deoxyribonucleotides and ribonucleotides utilized in obtaining such clones and in achieving expression of human factor VIII:C. This invention also relates to human AHF and its production by recombinant DNA techniques.

Factor VIII:C is a blood plasma protein that is defective or absent in Hemophilia A disease. This disease is a hereditary bleeding disorder affecting approximately one in 20,000 males. Factor VIII:C has also been known or referred to as factor VIII, the antihemophilic factor (AHF), antihemophilic globulin (AHG), hemophilic factor A, platelet cofactor, thromboplastinogen, and thrombocytolysin. It is referred to as "Factor VIII:C", to indicate that it is the compound which affects clotting activity. As used herein, "factor VIII:C" and "AHF" are synonymous.

Although the isolation of AHF from blood plasma has been described in the literature, the precise structure of AHF has not previously been identified, due in part to the unavailability of sufficient quantities of pure material, and the proteolytic nature of many contaminants and purification agents. While some quantities of impure AHF have been available as a concentrated preparation processed from fresh-frozen human plasma, the extremely low concentration of AHF in human plasma and the high cost of obtaining and processing human plasma make the cost of this material prohibitive for any extensive treatment of hemophilia.

The present method makes it possible to produce human AHF using recombinant DNA techniques.

AHF, like other proteins, is comprised of some twenty different amino acids arranged in a specific array. By using gene manipulation techniques, a method has been developed which enables production of AHF by identifying and cloning the gene which codes for the human AHF protein, cloning that gene, incorporating that gene into a recombinant DNA vector, transforming a suitable host with the vector which includes that gene, expressing the human AHF gene in such host, and recovering the human AHF produced thereby. Similarly, the present invention makes it possible to produce Porcine AHF by recombinant DNA techniques, as well as providing products and methods related to such porcine AHF production.

Recently developed techniques have made it possible to employ microorganisms, capable of rapid and abundant growth, for the synthesis of commercially useful proteins and peptides, regardless of their source in nature. These techniques make it possible to genetically endow a suitable microorganism with the ability to synthesize a protein or peptide normally made by another organism. The technique makes use of fundamental relationships which exist in all living organisms between the genetic material, usually DNA, and the proteins synthesized by the organism. This relationship is such that production of the amino acid sequence of the protein is coded for by a series of three nucleotide sequences of the DNA. There are one or more trinucleotide sequence groups (called codons) which specifically code for the production of each of the twenty amino acids most commonly occurring in proteins. The specific relationship between each given trinucleotide sequence and the corresponding amino acid for which it codes constitutes the genetic code. As a consequence, the amino acid sequence of every protein or peptide is reflected by a corresponding nucleotide sequence, according to a well understood relationship. Furthermore, this sequence of nucleotides can, in principle, be translated by any living organism. For a discussion of the genetic code, see J. D. Watson, *Molecular Biology of the Gene*, (W. A. Benjamin, Inc., 1977), the disclosure of which is incorporated herein by reference, particularly at 347–77; C. F. Norton, *Microbiology* (Addison, Wesley 1981), and U.S. Pat. No. 4,363,877, the disclosure of which is incorporated herein by reference.

The twenty amino acids from which proteins are made, are phenylalanine (hereinafter sometimes referred to as "Phe" or "F"), leucine ("Leu", "L"), isoleucine ("Ile", "I"), methionine ("Met", "M"), valine ("Val", "V"), serine ("Ser", "S"), proline ("Pro", "P"), threonine ("Thr", "T"), alanine ("Ala", "A"), tyrosine ("Tyr", "Y"), histidine ("His", "H"), glutamine ("Gln", "Q"), asparagine ("Asp", "N"), glutamic acid ("Glu", "E"), cysteine ("Cys", "C"), tryptophane ("Trp", "W"), arginine ("Arg", "R") and glycine ("Gly", "G"). The amino acids coded for by the various combinations of trinucleotides which may be contained in a given codon may be seen in Table 1:

TABLE 1

| First Position | \multicolumn{4}{c}{The Genetic Code Second Position} | Third Position |
|---|---|---|---|---|---|
| | T | C | A | G | |
| T | Phe | Ser | Tyr | Cys | T |
|   | Phe | Ser | Tyr | Cys | C |
|   | Leu | Ser | Stop* | Stop* | A |
|   | Leu | Ser | Stop* | Trp | G |
| C | Leu | Pro | His | Arg | T |
|   | Leu | Pro | His | Arg | C |
|   | Leu | Pro | Gln | Arg | A |
|   | Leu | Pro | Gln | Arg | G |
| A | Ile | Thr | Asp | Ser | T |
|   | Ile | Thr | Asp | Ser | C |
|   | Ile | Thr | Lys | Arg | A |
|   | Met | Thr | Lys | Arg | G |
| G | Val | Ala | Asp | Gly | T |
|   | Val | Ala | Asp | Gly | C |
|   | Val | Ala | Glu | Gly | A |
|   | Val | Ala | Glu | Gly | G |

*The "Stop" or termination codon terminates the expression of the protein.

Knowing the deoxyribonucleotide sequence of the gene or DNA sequence which codes for a particular protein allows the exact description of that protein's amino acid sequence. However, the converse is not true; while methionine is coded for by only one codon, the other amino acids can be coded for by up to six codons (e.g. serine), as is apparent from Table 1. Thus there is considerable ambiguity in predicting the nucleotide sequence from the amino acid sequence.

In sum, prior to the present invention, very little was known about the structure of AHF, and, despite substantial work over many years, those skilled in this art were unable to determine the structure of AHF, or of its gene, or provide any procedure by which AHF could be produced in substantially pure form in substantial quantities.

The method described herein by which the gene for human AHF is cloned and expressed includes the following steps:

(1) Purification of porcine AHF;
(2) Determination of the amino acid sequence of porcine AHF;
(3) Formation of oligonucleotide probes, and use of those probes to identify and/or isolate at least a fragment of the gene which codes for porcine AHF;
(4) Use of the porcine AHF gene fragment to identify and isolate human genetic material which codes for human AHF; (5) Using the previously described AHF DNA fragments to determine the site of synthesis of AHF from among the various mammalian tissues; (6) Producing cDNA segments which code for human and porcine AHF, using messenger RNA obtained from the tissue identification in step 5; (7) Constructing full length human and porcine cDNA clones from the cDNA segments produced in step 6, e.g. by ligating together cDNA segments which were cut by the same restriction enzymes; (8) Forming DNA expression vectors which are capable of directing the synthesis of AHF; (9) Transforming a suitable host with the expression vectors bearing the full length cDNA for human or porcine AHF; (10) Expressing human or porcine AHF in the host; and (11) Recovering the expressed AHF.

In the course of this work, a new technique of screening a genomic DNA library has been developed utilizing oligonucleotide probes based on the amino acid sequences contained in the AHF molecule.

The invention includes the above methods, along with the various nucleotides, vectors, and other products made in connection therewith.

BRIEF SUMMARY OF THE DRAWINGS

FIG. 1 is a depiction of the amino acid sequence for the amino terminal sequence of the 69,000 dalton thrombin cleavage product described in Example 1, as compared with the porcine AHF exon described in Example 3, and the human AHF exon described in Example 4.

FIG. 2 illustrates the amino acid sequences of bovine thrombin digestion fragments of (A) the amino terminus and (B) a 40 Kd thrombin cleavage product of the 166 Kd porcine AHF fragment isolated by Fass et al., infra.

FIG. 3 illustrates the design of an oligonucleotide probe for the identification and isolation of at least a portion of the porcine gene which codes for AHF.

FIG. 4 illustrates the DNA sequence for a DNA fragment (34-S1) which contains a porcine AHF exon as described in Example 6.

FIG. 5 is a representation of the DNA sequence of the Hae III insert bearing the exon for porcine AHF, as described in Example 3.

FIG. 6 is a representation of the DNA sequence for a portion of the Sau 3AI insert of clone 25-S1, showing a portion of the exon for human AHF, as described in Example 3.

DETAILED DESCRIPTION OF THE INVENTION

The following definitions are supplied in order to facilitate the understanding of this case. To the extent that the definitions vary from meanings circulating within the art, the definitions below are to control.

Amplification means the process by which cells produce gene repeats within their chromosomal DNA.

Cotransformation means the process of transforming a cell with more than one exogenous gene foreign to the cell, one of which confers a selectable phenotype on the cell.

Downstream means the direction going towards the 3' end of a nucleotide sequence.

An enhancer is a nucleotide sequence that can potentiate the transcription of genes independent of the identity of the gene, the position of the sequence in relation to the gene, or the orientation of the sequence.

A gene is a deoxyribonucleotide sequence coding for a given mature protein. For the purposes herein, a gene shall not include untranslated flanking regions such as RNA transcription initiation signals, polyadenylation addition sites, promoters or enhancers.

A selection gene is a gene that confers a phenotype on cells which express the gene as a detectable protein.

A selection agent is a condition or substance that enables one to detect the expression of a selection gene.

Phenotype means the observable properties of a cell as expressed by the cellular genotype.

Genotype means the genetic information contained within a cell as opposed to its expression, which is observed as the phenotype.

Ligation is the process of forming a phosphodiester bond between the 5' and 3' ends of two DNA strands. This may be accomplished by several well known enzymatic techniques., including blunt end ligation by T4 ligase.

Orientation refers to the order of nucleotides in a DNA sequence. An inverted orientation of a DNA sequence is one in which the 5' to 3' order of the sequence in relation to another sequence is reversed when compared to a point of reference in the DNA from which the sequence was obtained. Such points of reference can include the direction of transcription of other specified DNA sequences in the source DNA or the origin of replication of replicable vectors containing the sequence.

Transcription means the synthesis of RNA from a DNA template.

Transformation means changing a cell's genotype by the cellular uptake of exogenous DNA. Transformation may be detected in some cases by an alteration in cell phenotype. Transformed cells are called transformants. Pre-transformation cells are referred to as parental cells.

Translation means the synthesis of a polypeptide from messenger RNA.

The present method permits, for the first time, the identification and isolation of porcine Factor VIII:C gene by recombinant DNA techniques. It also permits, for the first time, the isolation and identification of the gene which encodes human factor VIII:C by recombinant DNA techniques, by taking advantage of the homology between porcine AHF DNA and human AHF DNA in order to locate and isolate the human gene for AHF. This route to cDNA clones for producing AHF via homology with the porcine AHF gene avoids the tedious time consuming and expensive need to purify human AHF, which is highly expensive and essentially unavailable.

Porcine AHF is first highly purified, most preferably by a monoclonal antibody purification technique such as that disclosed by David Fass et al, "Monoclonal Antibodies to Porcine AHF Coagulant and Their Use in the Isolation of Active Coagulent Protein", *Blood* 59: 594–600 (1982), and Knutsen et al., "Porcine Factor VIII:C prepared by affinity Interaction with Von Willebrand Factor and Heterologous Antibodies," *Blood*, 59: 615-24 (1982), the disclosures of both of which are incorporated herein by reference. Porcine factor VIII:C polypeptides are bound to anti-VIII:C monoclonal antibodies which are immobilized on a suitable affinity chromatography column. Two large molecular weight polypeptides, having molecular sizes of about 166 and 130 Kd, are eluted with ethylenediamine tetraacetic acid. Another protein segment having a molecular weight of about 76 Kd, is then eluted from the column, utilizing about 50% ethylene glycol. The amino acid sequences of these polypeptides, and/or of fragments of these polypeptides obtained in known manner, e.g. from enzymatic digestion of the proteins, using bovine thrombin or other suitable agents to break up the proteins, are then determined by known methods of analysis. Based on the amino acid sequence of these materials, oligonucleotide probes are synthesized, at least some of which will hybridize with DNA segments which code for the corresponding segment of AHF. These oligonucleotides are then used to screen for segments of the gene which code for porcine AHF.

Once all or a significant portion of the porcine gene for AHF is obtained, that recombinant material is used to screen a human genomic DNA library to locate and isolate the gene which codes for human AHF. In this procedure, it is established that there are substantial similarities between human AHF and porcine AHF, and advantage is taken of those similarities to isolate and identify the human factor VIII:C gene or gene segments.

The similarities in the porcine and human proteins are attributable to corresponding similarities in the DNA sequences which code for the amino acid sequences. The genetic materials coding for the AHF proteins in humans and pigs are identical at a high percentage of positions, and thus exhibit hybridization when subjected to the procedure of, for example, Benton and Davis, the disclosure of which is incorporated herein by reference.

Once the full length human or porcine AHF cDNA clone is obtained, known and appropriate means are utilized to express the AHF protein, e.g. insertion into an appropriate vector, and transfection into an appropriate host, selection of transformed cells (transformants), and culture these transformants, to express AHF activity.

Host-vector systems for the expression of AHF may be procaryotic, but the complexity of AHF makes the preferred expression system (at least for biologically-active AHF having clotting activity) a mammalian one. This is easily accomplished by eucaryotic (usually mammalian or vertebrate cells) transformation with a suitable AHF vector. Eucaryotic transformation is in general a well-known process, and may be accomplished by a variety of standard methods. These include the use of protoplast fusion, DNA microinjection, chromosome transfection, lytic and nonlytic viral vectors (For example, Mulligan et al., "Nature" (London) 277:108-114 [1979], cell-cell fusion (Fournier et al., "Proc. Nat. Acad. Sci." 74:319-323 [1977], lipid structures (U.S. Pat. No. 4,394,448) and cellular endocytosis of DNA precipitates (Bachetti et al., "Proc. Nat. Acad. Sci. 74:1590-1594 [1977]).

Transformation which is mediated by lytic viral vectors is efficient but is disadvantageous for a number of reasons: The maximum size of transfected DNA is limited by the geometry of viral capsid packing, the exogenous genes are frequently deleted during viral replication, there is a requirement for helper virus or specialized hosts, host cells must be permissive, and the hosts are killed in the course of the viral infection.

Nonlytic transformations are based on the transcription and translation of virus vectors which have been incorporated into a cell line as a stable episome. These systems generally require unique cell lines and suffer from a number of disadvantages. See "Trends in Biochemical Sciences", June 1983, pp. 209-212.

On the other hand, other transformation methods in which extrachromosomal DNA is taken up into the chromosomes of host cells have been characterized by low frequencies of transformation and poor expression levels. These initial difficulties were ameliorated by transformation with genes which inheritably confer selectable phenotypes on the small subpopulation of cells that are in fact transformed (selection genes). The entire population of transformed cells can be grown under conditions favoring cells having acquired the phenotype, thus making it possible to locate transformed cells conveniently. Thereafter, transformants can be screened for the capability to more intensely express the phenotype. This is accomplished by changing a selection agent in such a way as to detect higher expression.

Selection genes fall into three categories: Detectably amplified selection genes, dominant selection genes, and detectably amplified dominant selection genes.

Detectably amplified selection genes are those in which amplification can be detected by exposing host cells to changes in the selection agent. Detectably amplified genes which are not dominant acting generally require a parental cell line which is genotypically deficient in the selection gene. Examples include the genes for hydroxymetholglutanyl CoA reductase (Sinensky, "Biochem. Biophys. Res. Commun" 78:863 [1977], ribonucleotide reductase (Meuth et al. "Cell:3:367 [1943], aspartate transcarbamylase; (Kemp et al. "Cell" 9:541 [1976], adenylate deaminase (DeBatisse et al. "Mol and Cell Biol." 2(11):1346-1353 [1982] mouse dihydrofolate reductase (DHFR) and, with a defective promoter, mouse thymidine kinase (TK).

Dominant selection genes are those which are expressed in transformants regardless of the genotype of the parental cell. Most dominant selection genes are not detectably amplified because the phenotype is so highly effective in dealing with the selection agent that it is difficult to discriminate among cell lines that have or have not amplified the gene. Examples of dominant selection genes of this type include the genes for procaryotic enzymes such as xanthine-guanine phosphoribosyltransferase (Mulligan et al. "Proc. Nat. Acad. Sci." 78[4]:2072-2076 [1981] and aminoglycoside 3'-phosphotransferase (Colbere-Garapin et al., "J. Mol. Biol.", 150:1-14 [1981].

Some dominant selection genes also are detectably amplified. Suitable examples include the mutant DHFR gene described by Haber et al., "Somatic Cell Genet." 4:499-508 (1982), cell surface markers such as HLA antigens and genes coding for enzymes such as specific esterases that produce fluorescent or colored products from fluorogenic or chromogenic substrates as is known in the art.

Detectably-amplified, dominant selection genes are preferred for use herein. It should be understood that a dominant selection gene in some cases can be converted to a detectably amplified gene by suitable mutations in the gene.

Selection genes at first were of limited commercial utility. While they enabled one to select transformants having the propensity to amplify uptaken DNA, most selection genes produced products of no commercial value. On the other hand, genes for products which were commercially valuable generally did not confer readily selectable (or even detectable) phenotypes on their transformants. This would be the case, for example, with enzymes or hormones which do not provide transformed cells with unique nutrient metabolic or detoxification capabilities. Most proteins of commercial interest fall into this group, e.g. hormones, proteins participating in blood coagulation and fibrinolytic enzymes.

Subsequently it was found that eucaryotic cells having the propensity to be transformed with and amplify the selection gene would do the same in the case of the product gene. By following the selection gene one could identify a subpopulation of transformant cells which coexpress and coamplify the product gene along with the selection gene. It has been the practice to culture the transformants in the presence of the selection agent and to conclude that transformants having increased expression of the selection gene will also show increased expression of the product gene. This is not always the case, as will be more fully explored below. Axel et al. (U.S. Pat. No. 4,399,216) use the term cotransformation to describe the process of transforming a cell with more than one different gene, whether by vector systems containing covalently linked or unlinked genes, and in the latter case whether the genes are introduced into host cells sequentially or simultaneously. Cotransformation should "allow the introduction and stable integration of virtually any defined gene into cultured cells" (Wigler et al. "Cell", 16:777–785, [1975]), and "by use of the cotransformation process it is possible to produce eucaryotic cells which synthesize desired proteinaceous and other materials" (U.S. Pat. No. 4,399,216, column 3, lines 37–42).

Transformation Vectors

Vectors used in AHF cotransformation will contain a selection gene and the AHF gene. In addition there usually will be present in the transformation or cotransformation vectors other elements such as enhancers, promoters, introns, accessory DNA, polyadenylation sites and 3' noncoding regions as will be described below.

Suitable selection genes are described above. It is preferred that the selection agent be one that prevents cell growth in the absence of the selection gene. That way, revertant cells in large scale culture that lose the selection gene (and presumably the AHF gene as well) will not over-grow the fermentation. However, it would be desirable in the commercial production of AHF to avoid the use of cell toxins, thereby simplifying the product purification steps. Thus, a desirable selection gene would be one that enables transformants to use a nutrient critical for growth that they otherwise would not be able to use. The TK gene described above is an example.

Two classes of vectors have been employed in cotransformation. The first class are the unlinked vectors. Here the selection gene and the AHF gene are not covalently bound. This vector class is preferred because the step of ligating or otherwise bonding the two genes is not required. This simplifies the transformation process hbecause the selection and product genes usually are obtained from separate sources and are not ligated in their wild-type environment. In addition, the molar ratio of the AHF and selection genes employed during cotransformation can be adjusted to increase cotransformation efficiency.

The second class of cotransformation vectors are linked vectors. These vectors are distinguished from unlinked vectors in that the selection and AHF genes are covalently bound, preferably by ligation.

The vectors herein may also include enhancers. Enhancers are functionally distinct from promoters, but appear to operate in concert with promoters. Their function on the cellular level is not well understood, but their unique characteristic is the ability to activate or potentiate transcription without being position or orientation dependent. Promoters need to be upstream of the gene, while enhancers may be present upstream or 5' from the promoter, within the gene as an intron, or downstream from the gene between the gene and a polyadenylation site or 3' from the polyadenylation site. Inverted promoters are not functional, but inverted enhancers are. Enhancers are cis-acting, i.e., they have an effect on promoters only if they are present on the same DNA strand. For a general discussion of enhancers see Khoury et al., "Cell" 33:313–314 (1983).

Preferred enhancers are obtained from animal viruses such as simian virus 40, polyoma virus, bovine papilloma virus, retrovirus or adenovirus. Ideally, the enhancer should be from a virus for which the host cell is permissive, i.e. which normally infects cells of the host type. Viral enhancers may be obtained readily from publically available viruses. The enhancer regions for several viruses, e.g., Rous sarcoma virus and simian virus 40, are well known. See Luciw et al., "Cell" 33:705–716 (1983). It would be a matter of routine chemistry to excise these regions on the basis of published restriction maps for the virus in question and, if necessary, modify the sites to enable splicing the enhancer into the vector as desired. For example, see Kaufman et al, "J. Mol. Biol.", 159:601–621 (1982) and "Mol. Cell Biol." 2(11):1304–1319 (1982). Alternatively, the enhancer may be synthesized from sequence data; the sizes of viral enhancers (generally less than about 150 bp) are sufficiently small that this could be accomplished practically.

Another element which should be present in the vector assembly is a polyadenylation splicing (or addition) site. This is a DNA sequence located downstream from the translated regions of a gene, shortly downstream from which in turn transcription stops and adenine ribonucleotides are added to form a polyadenine nucleotide tail at the 3' end of the messenger RNA. Polyadenylation is important in stabilizing the messenger RNA against degradation in the cell, an event that reduces the level of messenger RNA and hence the level of product protein.

Eucaryotic polyadenylation sites are well known. A concensus sequence exists among eucaryotic genes: The hexanucleotide 5'-AAUAAA-3' is found 11–30 nucleotides from the point at which polyadenylation starts. DNA sequences containing polyadenylation sites may be obtained from viruses in accord with published reports. Exemplary polyadenylation sequences can be obtained from mouse beta-globulin, and simian virus 40 late or early region genes, but viral polyadenylation sites are preferred. Since these sequences are known, they may be synthesized in vitro and ligated to the vectors in conventional fashion.

A polyadenylation region must be located downstream from either the AHF and/or selection gene, but may be ligated to either gene. It may be ligated to the selection gene only, and not the product gene, and this will be the case whether the vectors are linked or unlinked. The sequence which separates the polyadenylation site from the translational stop codon is preferably an untranslated DNA oligonucleotide such as an unpromoted eucaryotic gene. Since such oligonucleotides and genes are not endowed with a promoter they will not be expressed. The oligonucleotide should extend for a considerable distance, on the order of up to about 1,000 bases, from the stop codon to the polyadenylation site. This 3' untranslated oligonucleotide generally results in an increase in product yields. The vector may terminate from about 10 to about 30 bp downstream from the concensus sequence, but it is preferable to retain the 3' sequences found downstream from the polyadenylation site in its wild-type environment. These sequences typically extend about from 200 to 600 base pairs downstream from the polyadenylation site.

The vectors described herein may be synthesized by techniques well known to those skilled in this art. The components of the vectors such selection genes, enhancers, promoters, and the like may be obtained from natural sources or synthesized as described above. Basically, if the components are found in DNA available in large quantity, e.g. components such as viral functions, or if they ,ay be synthesized, e.g. polyadenylation sites, then with appropriate use of restriction enzymes large quantities of vector may be obtained by simply culturing the source organism, digesting its DNA with an appropriate endonuclease, separating the DNA fragments, identifying the DNA containing the element of interest and recovering same. Ordinarily, a transforration vector will be assembled in small quantity and then ligated to a suitable autonomously replicating synthesis vector such as a procaryotic plasmid or phage. The pBR322 plasmid may be used in most cases. See Kaufman et al., op. cit.

The synthesis vectors are used to clone the ligated transformation vectors in conventional fashion, e.g. by transfection of a permissive procaryotic organsim, replication of the synthesis vector to high copy number and recovery of the synthesis vector by cell lysis and separation of the synthesis vector from cell debris.

The resulting harvest of synthesis vector may be directly transfected into eucaryotic cells, or the transformation vector may be rescued from the synthesis vector by appropriate endonuclease digestion, separation by molecular weight and recovery of the transformation vector. Transformation vector rescue is not necessary so long as the remainder of the synthesis vector does not adversely affect eucaryotic gene amplification, transcription or translation. For example, the preferred synthesis vector herein is a mutant of the E. coli plasmid pBR322 in which sequences have been deleted that are deleterious to eucaryotic cells. See Kaufman et al., op. cit. Use of this mutant obviates any need to delete the plasmid residue prior to cotransformation.

Cotransformation, Selection and Detection of Amplification

The cells to be transformed may be any eucaryotic cell, including yeast protoplasts, but ordinarily a nonfungal cell. Primary explants (including relatively undifferentiated cells such as stem cells), and immortal and/or transformed cell lines are suitable. Candidate cells need not be genotypically deficient in the selection gene so long as the selection gene is dominant acting.

The cells preferably will be stable mammalian cell lines as is discussed above. Cell lines that are known to stably integrate selection genes into their chromosomal DNA are best, for example Chinese hamster ovary (CHO) cell lines. Also useable are HeLa, COS monkey cells, melanoma cell lines such as the Bowes cell line, mouse L cells, mouse fibroblasts and mouse NIH 3T3 cells.

Cotransformation with unlinked vectors may be accomplished serially or simultaneously, (see U.S. Pat. No. 4,399,216). Methods for facilitating cellular uptake of DNA are described above. Microinjection of the vector into the cell nucleus will yield the highest transformation efficiencies, but exposing parental cells to DNA in the form of a calcium phosphate precipitate is most convenient. Considerably better cotransformation efficiencies result from cotransformation with a molar excess of product to selection gene, on the order of 100:1.

The population of cells that has been exposed to transforming conditions is then processed to identify the transformants. Only a small subpopulation of any culture which has been treated for cotransformation will exhibit the phenotype of the selection gene. The cells in the culture are screened for the phenotype. This can be accomplished by assaying the cells individually with a cell sorting device where the phenotype is one that will produce a signal, e.g. fluorescence upon cleavage of a fluorogenic substrate by an enzyme produced by the selection gene. Preferably, however, the phenotype enables only transformants to grow or survive in specialized growth media as is further discussed above.

Selection transformants then will be screened for ligation of the product gene into their chromosomes or for expression of the product itself. The former can be accomplished using Southern blot analysis, the latter by standard immunological or enzymatic assays.

Once the tranformants have been identified, steps are taken to amplify expression of the product gene by further cloning in the presence of a selection agent such as MTX. See U.S. Pat. No. 4,399,216.

Cotransformants which may be produced in accordance with the processes described herein are suitable for in vivo transfections of higher organisms in accordance with known techniques. Primary explants or stable cell lines from a potential host animal are cotransformed and inoculated into the host or a substantially otherwise syngeneic host which is genotypically deficient in the product protein.

The invention will be further understood with reference to the following illustrative embodiments, which are purely exemplary, and should not be taken as limitive of the true scope of the present inevntion, as described in the claims.

Unless otherwise noted, restriction endonucleases are utilized under the conditions and in the manner recommended by their commercial suppliers. Ligation reactions are carried on as described by Maniatis et al., supra at 245–6, the disclosure of which is incorporated herein by reference, using the buffer described at page 246 thereof and using a DNA concentration of 1–100 ug/ml, at a temperature of 23° C. for blunt ended DNA and 16° C. for "sticky ended" DNA. "Phosphatasing" as described herein, refers to dephosphorylation of DNA, and is carried out in the manner described by Maniatis et al., supra, e.g. at page 133 et seq. "Kinasing" refers to phosphorylation of DNA. Electrophoresis is done in 0.5-1.5% Agarose gels containing 90 mM Tris-borate, 10 mM EDTA. "Nick-translating" refers to the method for labeling DNA with 32 p as described by Rigby et al., *J. Mol. Biol.*, 113:237 (1977). All radiolabeled DNA is labeled with 32 p, whatever labeling technique was used.

By "rapid prep" is meant a rapid, small scale production of bacteriophage or plasmid DNA, e.g., as described by Maniatis et al., supra, at p. 365-373.

EXAMPLE 1. PROTEIN SEQUENCE ANALYSIS

Porcine factor VIII:C was purified by Dr. David Fass according to published procedures Knutsen and Fass (1982); Fass et al. (1982), supra. Amino acid sequence analysis is performed on a bovine thrombin digest product of the 76,000 dalton protein as described below.

Porcine AHF polypeptides bound to the anti-VIII:C monoclonal antibody column, can be sucessively eluted in two steps (Fass et. al. 1982). The two larger molecular weight species, 166,000 and 130,000 daltons, can be eluted with EDTA. The remaining polypeptide, having a molecular weight of about 76,000 daltons, can then be eluted with 50% ethylene glycol.

The 76,000 dalton protein is digested with thrombin after extensive dialysis in 50 mM Tris-HCl (pH 7.5), 0.15 M NaCl. Bovine thrombin digests are performed at room temperature for 60 minutes using 1 unit/ml of bovine thrombin, followed by the addition of another 1 unit/ml thrombin and incubation for an additional 60 minutes. The thrombin digestions are terminated by heating for 10 minutes at 90° C. in 0.01% SDS. The major thrombin digest product of the 76,000 dalton protein is a polypeptide, 69,000 daltons (69 Kd).

Less than 1 μg of the 69 Kd polypeptide species described above is iodinated to serve as a radioactive marker after SDS gel electrophoresis, in accordance with the procedure of U. K. Laemmli, *Nature*, 227:680 (1970), the disclosure of which is incorporated herein by reference. The polypeptide, dissolved in TAS buffer (50 mM Tris-acetate (pH 7.8), 0.1% SDS) is added to 100 μl of the same buffer containing 5 mCi of carrier-free iodine-125. 50 μl of 2.5 mg/ml chloramine T (Baker) in TAS buffer are added and the solution agitated for 1 minute. The reactions are stopped by adding 50 μl 2.5 mg/ml sodium metabisulfate in TAS buffer followed by 1 minute agitation. Labeled protein is separated from unincorporated I$^{125}$ by chromatography using a small volume Sephadex G-25 M column (PD 10, Pharmacia). The column is pre-equilibrated with several column volumes of TAS buffer containing 2.5 mg/ml sodium iodide. The void volume is collected and protein integrity analyzed by SDS gel electrophoresis in accordance with the procedures of Laemmli, (1970), supra.

The radioactively labeled 69 Kd protein is added to its unlabeled counterpart for subsequent monitoring. The protein is then individually electrophoretically concentrated. The protein solutions are adjusted to 0.1% SDS, 10 mM dithiothreitol and Coomassie brilliant blue (Serva) are added to make the solution a very pale blue.

The solutions are then dialyzed briefly (1-2 hours) in TAS buffer using Spectrapore dialysis tubing (made by Spectrum Medical Industries, Inc., with molecular weight cut off at about 14,000). The dialyzed protein samples are then placed in an electrophoretic concentrator, of the design suggested by Hunkapiller, et al *Meth. Enzymol.*, Enzyme Structures, Part I, 91:227 (1983), and electrophoretically concentrated in TAS buffer for 24 hours at 50 volts.

The 69 Kd AHF polypeptide, concentrated by the above procedure, is electrophoresed through an SDS-polyacrylamide gel in accordance with Laemmli, supra. The purified protein, identified by autoradiography of the radioactively labeled tracer polypeptide, is excised from the gel and electroeluted and concentrated as descibed by Hunkapiller et al., supra. The concentrated sample is suitable for direct amino acid sequence analysis using the gas phase sequenator as described in Hewick et al., *J. Biol. Chem.* 256:7990 (1981).

The amino terminal sequence of the 69,000 dalton thrombin cleavage product is as depicted in FIG. 1. The amino acid sequences of (A) the amino terminus and (B) a 40 kd bovine thrombin digestion product from the 166 kd AHF fragment noted by Fass et al., supra, are shown in FIG. 2.

EXAMPLE 2

Chemical Synthesis of Oligonucleotide Probes for a Porcine AHF Gene (a) Pentapeptide Probe Pool The partial amino acid sequence of a fragment of porcine AHF having been determined allows porcine AHF oligonucleotide probes to be designed and synthesized. From the genetic code (Table 1) it is possible to predict the gene sequence that codes for this sequence of amino acids. Because the genetic code is degenerate, there are more than one possible DNA coding sequences for each amino acid sequence. Accordingly, a plurality or pool of complementary oligonucleotide probe sequences are provided for a region of the AHF molecule which required only a reasonable number of oligonucleotides to ensure the correct DNA sequence. Such regions are selected by searching for tracks of five to eight contiguous amino acids which have the lowest degeneracy. After the region is selected, a pool of oligonucleotides is synthesized, which would include all possible DNA sequences which could code for the five to eight amino acids in the selected region.

In the 69,000 dalton thrombin-cleavage fragment of porcine AHF there is a pentapeptide sequence running from the 18th through the 22nd amino acid from the amino terminus, which could be coded for by up to 16 different DNA sequences, each having five codons, for a length of 15 nucleotides.

```
                           18      20       22
                          Trp—Asp—Tyr—Gly—Met
        Possible mRNA Sequences  UGG GAU UAU GGU AUG
                                  or  or  or
                                     GAC UAC GGC
                                              or
                                             GGA
                                              or
                                             GGG
```

The probes are made by synthesizing a limited number of mixtures of oligonucleotides with two to eight or more oligonucleotides per mixture. These mixtures are referred to as pools. Enough pools are made to encompass all possible coding sequences.

These oligonucleotides can be synthesized manually, e.g., by the phospho-tri-ester method, as disclosed, for example in R. L. Letsinger, et al., *J. Am. Chem. Soc.* 98:3655 (1967), the disclosure of which is incorporated by reference. Other methods are well known in the art. See also Matteucci and Caruthers, *J. Am. Chem. Soc.* 103:3185 (1981), the disclosure of which is incorporated by reference.

Preferably, however, the synthetic oligonucleotide probes for the desired polypeptide sequences are prepared by identical chemistry with the assistance of the completely automatic Applied Biosystems DNA synthesizer, Model 380A, as indicated above.

The oligonucleotides thus prepared can then be purified on a reverse HPLC column, as described by H. Fritz, et al., *Biochemistry*, 17:1257 (1978), the disclosure of which is incorporated herein by reference. After detritylation with 80% HOAc, the resulting oligonucleotide is normally pure and can be used directly as a probe. If there are any contaminants, the synthetic DNA can be further purified on the same HPLC column, preferably using a slightly different gradient system.

Oligonucleotides are labelled, e.g. by using [=$^{32}$P]ATP and T4 polynucleotide kinase, and their sequence checked either by two-dimensional homochromatography as described by Sanger et al., *PNAS U.S.A.* 70:1209 (1973) or by the Maxam-Gilbert method, *Meth. Enzymology*, 65:499 (1977), the disclosures of both of which are incorporated herein by reference.

(b) Forty Five Nucleotide Probes

A unique aspect of the present invention has been the use of oligonucleotide probes to screen a genomic DNA library for the AHF gene or fragments thereof. While oligonucleotides have been used for screening of cDNA libraries, see, e.g. M. Jaye, et al, *Nucleic Acids Research* 11:2325 (1982), the disclosure of which is incorporated herein by reference, genomic libraries have previously been screened successfully only with cDNA probes, i.e. probes which were generated only after the tissue source of the mRNA for a described protein had been identified and utilized to generate a cDNA clone which precisely matched the DNA sequence of the gene sought by the genomic search.

In the present case, it has been shown possible to use oligonucleotides to identify gene segments in a genomic library which code for the amino acid sequence of the proteins of interest, and identification of such gene segments provides an exact probe for use in mRNA, cDNA or further genomic screening techniques.

Preferably, as here, oligonucleotides corresponding to at least two segments of the amino acid sequence of the protein of interest are utilized. Preferably at least one of the oligonucleotide probes is used in the form of one or more pools of oligonucleotides which in the aggregate include every possible DNA sequence which could code for the amino acid sequences selected. Preferably one relatively short probe, e.g. 11 to 25 nucleotides, preferably 15 to 20 nucleotides is utilized in conjunction with a relatively long probe, e.g. 30 to 200 nucleotides, preferably 40 to 50 nucleotides. The second probe can be used for confirmation, and is not always necessary for identification of the DNA segment. Preferably at least one of the probes, and more preferably the longer of the probes is designed in accordance with the Rules 1 to 4 described below.

Rule 1. Codon Preference    In the absence of other considerations, the nucleotide sequence was chosen which matched prevailing or similar sequences in similar mammalian genes. See *Mechanisms of Ageing Dev.*, 18:(1982).

Rule 2. Advantageous GT Pairing    The nucleotide G, in addition to bonding to its compliment C, can also form weak bonds with the nucleotide T. See K. L. Agarwal et al., *J. Biol. Chem.* 256:1023 (1981). Thus, faced with a choice of G or A for the third portion of an ambigious codon, it is preferable to choose G, since if the resulting hybridization would occur even if the actual nucleotide in the position is a T, rather than a C, the hybridization would still be stable. If an A were chosen incorrectly, the corresponding A:C incompatability could be enough to destroy the ability of the probe to hybridize with the genomic DNA.

Rule 3. Avoidance of 5'CG Sequences When selecting from among the possible ambiguities, select those nucleotides which will not contain the 5'$C_p$G sequence, either intra codon or inter codon.

Rule 4. Mismatch Position    In choosing the codon sequences to use, consideration was given to the postulation that mismatches near the ends of the molecule do not adversely affect that codon was close to the center of the probe, the tendency was to test a pool of possible nucleotide sequences for that codon, whereas codon positions near the ends of the probe were more likely to be subject to determinations on the basis of codon preference.

The chosen sequence for the 45-mer probes, as well as the amino acid sequences, the possible DNA sequences, and the "Actual Probe Sequence", i.e. the complement of actual coding strand determined for the AHF exon, as shown in FIG. 3.

Thus, out of nucleotide positions involving choices, three were covered by using pools containing both possible nucleotide alternatives, five were predicted correctly, one was predicted in a way to maintain neutrality though incorrect, and four others were in error.

Despite the approximately 11% mismatch (5/45) the pool of 45-mer oligonucleotides are adequate to strongly identify a porcine AHF gene fragment, as described below.

EXAMPLE 3. SCREENING OF PORCINE GENOMIC LIBRARY

A porcine genomic library is constructed using the bacteriophage vector Lambda Jl. Lambda Jl is derived from L47.1 (Loenen et al., *Gene* 20:249 (1980)) by replacement of the 1.37 kb and 2.83 kb Eco RI-Bam HI fragments with a 95 bp Eco Rl-Hind III-Xba I-Bgl II-Bam HI polylinker. The 6.6 kb Bam HI fragment is then present as a direct repeat in reverse orientation relative to L47.1. The cloning capacity for Bam HI fragments is 8.6–23.8 kb. Bam HI cleaved porcine DNA (prepared as described by Piccini et al., *Cell*, 30:205 (1982)) is phenol extracted, ethanol precipitated and concentrated by centrifugation in a Microfuge. 0.67 $\mu$g of Bam HI porcine DNA is ligated to 2 $\mu$g of Lambda Jl Bam HI "arms", prepared as described in Maniatis, et al., supra, pp 275–279, in a volume of 10 $\mu$l ligation buffer with 10 units T4 DNA ligase (Maniatis et al., supra, p 474). The ligated DNA is packaged and plated as described in Maniatis et al., supra, p 291.

Approximately $4 \times 10^5$ pfu are plated on *E. coli* stain C600 on 15 cm plastic petri plates containing NZCYM agarose, at 8,000 pfu/plate. These recombinant phage are screened by the method of Woo (1979) using the 45-mer probe described above, radioactively labeled with 32P as described above, as a probe. Filters are then hybridized in 5xSSC, 5x Denhardt's, 0.1% SDS, and $5 \times 10^6$ cpm/ml probe at 45° C. for 16 hours, washed in 5 x SSC, 0.1% SDS at 50° C. and subjected to autoradiography using intensifying screens (DuPont Lightning-Plus). Autoradiography reveals numerous phage which hybridized, to varying degrees, with the 45-mer. The filters are then denatured in 0.5M NaOH, neutralized in 1.0M Tris pH7.5, 1.5M NaCl and hybridized to the 15-mer as described for the 45-mer except the hybridization and washing temperature is 37° C. One phage which hybridized to both probes is picked from the original plate and 100 pfu plated and the plaques screened as described above using the 15-mer as probe.

A positive phage, named PB34, is picked as a plug and used to make a plate lysate as described in Maniatis et al, supra, pp 65–66. A small-scale isolation of PB34 DNA is achieved using the procedure described in Maniatis et al., supra, pp 371–372. 10μl of this DNA was cut with the restriction enzyme Hae III and then phosphatased using calf alkaline phosphatase (Boehringer-Mannheim). The DNA sequence, called 34 HI, is shown in FIG. 5. After phenol extraction, 20 ng of Sma I cut M13mp8 DNA is added, the solution is made 0.2M NaCl and nucleic acid precipitated by the addition of 2 volumes ethanol. Precipitated DNA is pelleted by centrifugation and redissolved in 2 μl of a ligation mixture and the DNA is ligated for 30 minutes at 23° C., diluted to 50 μl with ligase buffer and ligated an additional 3 hours. 5 μl of this reaction is used to transform *E. coli* strain JM101/TG1.

Cells are made competent for transformation by growing to an O.D.$_{600}$ of 0.5 at 37° C. in 50 ml SOBM media (SOBM is 2% tryptone, 0.5% yeast extract, 0.1 M NaCl, 0.11 g KOH per liter, 20 mM MgSo$_4$). Cells are pelleted by centrifugation at 2500 rpm for 10 minutes at 4° C. The cells are resuspended in 3.5 ml 100 mM RbCl, 45 mM MnCl$_2$, 50 mM CaCl$_2$, 10 mM potassium MES pH 6.4 (MES=methylethane sulfonic acid). 200μl of competent cells are transformed with the DNA contained in 5 ml of the ligation reaction at 0° C. for 30 minutes. The cells are then heat-shocked at 42° C. for 90 seconds after which 4 ml of 0.8% agarose/SOBM containing 100 μl stationary JM101/TG1 cells are added and plated on 10 cm SOBM agar petri plates.

A subclone hybridizing to the 15 mer is identified by screening using the procedure of Benton and Davis. This clone is isolated and prepared for use as a template. M13 template DNA is prepared by growing 1.5 ml of infected cells 5 hours at 37° C. Cells are pelleted by centrifugation for 10 minutes in a Beckman microfuge. 1.0 ml of supernatant (containing virus) is removed isolated and prepared for use as a template. M13 template DNA is prepared by growing 1.5 ml of infected cells 5 hours at 37° C. Cells are pelleted by centrifugation for 10 minutes in a Beckman microfuge. 1.0 ml of supernatant (containing virus) is removed and 200 μl of 20% polyethylene glycol, 2.5 M NaCl is added This sample is then incubated at room temperature for 15 minutes followed by centrifugation for 5 minutes in a Beckman microfuge. The pellet is dissolved in 100 μl TE, 7.5 μl of 4M NaCHCOO pH 4.5 is added and the sample extracted twice with a 1:1 mixture of phenol-chloroform and once with chloroform. The single-stranded phage DNA is then precipitated by the addition of 2 volumes of ethanol. Precipitated DNA is pelleted by centrifugation in a Beckman microfuge and dissolved in 30 μl 1 mM Tris pH 8.0, 0.1 mM EDTA. The DNA sequencing is performed by the dideoxy chain termination technique, see, e.g. Sanger et al., *PNAS U.S.A.*, 74:5463 (1977), utilizing the 15-mer as a primer. The sequence observed confirmed the subclone as containing a porcine AHF exon, since it encludes the identical 14 amino acids encompassed by the region phenylalanine$_2$ to glutamine$_{15}$ in the 69K fragment. Further confirmation came from sequencing the 5' end of the Hae III insert in the 34-Hl vector, by priming with the "Universal primer" (Bethesda Research Labs) at a point adjacent the polylinker in that vector. Also, the insert from this clone, named 34-HI, was recloned into M13mp9 by restricting the DNA with Eco RI and Hind III, phosphatasing with calf alkaline phosphatase, and ligating to Eco RI, Hind III cleaved M13mp9 DNA. This clone, which contains an inversion of the Hae segment relative to the universal primer, was also described above. The resulting sequence data is shown in FIG. 6. This sequence confirms that this subclone contains an exon of the porcine AHF gene that could encode at least the thirty amino acids from the phenylanine$_2$ through arginine$_{31}$ of the 69K fragment (FIG. 1).

It appears likely that arginine$_{31}$ borders an intron because termination codons can be found downstream from that location in all three reading frames, and a sequence similar to the consensus splice donor sequence (C(or A)AG/TA(or G)AGT) is also found in that region. Further, the amino acid sequence which would be encoded by the downstream DNA differs completely from that observed in the 69 Kd fragment of porcine AHF.

PB34 DNA was cut with Bam HI and electrophoresed through an agarose gel and the bands visualized by ultraviolet light after staining the gel in 5 μg/ml ethidium bromide. Three inserts of approximately 6.6 kb, 6.0 kb, and 1.8 kb were observed. The DNA in the gel was transferred to nitrocellulose as described in Maniatis et al., supra, pp 383–386. Hybridization of the filter to the 15-mer and autoradiography were performed as described above. Autoradiography revealed that the 6.0 kb band contained an AHF gene fragment which hybridized to the 15-mer probe.

Thus, for the first time, a section of the gene coding for porcine AHF had been isolated and identified. A bacteriophage lambda recombinant clone containing PB 34 is on deposit at the American Type Culture Collection under Accession Number ATCC 40087.

EXAMPLE 4. LOCATION OF HUMAN AHF GENE

The human genomic library described by Maniatis et al., *Cell*, 15:687 (1978) is screened for the human AHF gene by infecting E. coli strain LE392 (publicly available) with $6 \times 10^5$ pfu and plating on 15 cm NZCYM agar plates at a density of 20,000 pfu/plate. These phage are screened using the procedure of Benton and Davis with the 6.0 kb porcine AHF fragment described in Example 3, labeled with $^{32}$P by nick translation, as the probe. A phage exhibiting a strong hybridization signal is picked and plated at about 100 pfu/10 cm plate and screened in duplicate as described above using the radioactively labeled 45-mer as one probe and the 6.0 kb Bam HI fragment of PB34 as the other. A phage, named HH25, which hybridizes to both probes is identified, a plate stock made and rapid prep DNA prepared as described above. The phage DNA is cut with Sau 3aI, phosphatased with calf alkaline phosphatase phenol extracted, and co-precipitated with 20 ng of Bam HI cut M13 mp8 DNA. Precipitated DNA is pelleted by centrifugation and redissolved in 2 µl ligase buffer containing T4 DNA ligase. Ligation is performed for 2 minutes at 16° C., diluted to 50 µl in ligase buffer containing T4 DNA ligase and incubated an additional 3 hours at 16° C. 5 µl of this reaction mixture is used to transform E. coli strain JM101/TG1 as described in Example 3 above.

The plaques are screened using the Benton and Davis procedure and probing with radioactively labeled 15-mer. A phage plaque, named 25-S1, exhibiting hybridization is isolated and single-stranded phage DNA prepared for use as a DNA sequencing template as described above. Sequencing is performed using the dideoxy chain termination technique described by Sanger et al., supra, utilizing the 15 mer as primer, and gives the information strand DNA sequence shown in FIG. 6. 84 nucleotides sequenced in this manner demonstrated 85% homology with the homologous region of porcine AHF. There is also only one amino acid difference between the porcine AHF 69K region 2-16 and that was predicted from the human nucleotide sequence of FIG. 6. This high degree of homology shows that the DNA of the recombinant phage HH-25 emanates from the AHF gene.

Thus, for the first time, an exon for the human AHF gene has been isolated and identified. A bacteriophage lambda recombinant clone containing HH 25 is on deposit at the American Type Culture Collection under the Accession Number ATCC 40086.

EXAMPLE 5: IDENTIFYING CELLS ACTIVELY TRANSCRIBING AHF

The porcine and human AHF exons described above are useful for a variety of functions, one of which is as a screening agent which permits identification of the tissue which is the site of synthesis of AHF in vivo. A number of screening methods are available, based on the use of the exon as an exact complement to the mRNA which is produced during the course of natural expression of AHF. In the screening procedures, tissue from various parts of the body is treated to liberate the mRNA contained therein, which is then hybridized to a DNA segment containing the exon for AHF, and if a molecule of mRNA does hybridize to that exon, the tissue which is the source of that mRNA is the source of AHF.

1. Screening Procedure

Porcine tissue from various organs, including kidneys, liver, pancreas, spleen, bone marrow, lymph nodes, etc., is prepared by guanidine hypochloride extraction as described by Cox *Methods Enzymol,* 12B:120 (1968), the disclosure of which is incorporated herein by reference, with some modifications. Briefly, tissue is explanted into 8 M guanidine hydrochloride, 50 mM Tris (pH 7.5), 10 mM EDTA and homogenized in an Omnimixer (Sorvall) at top speed for 1 minute. The homogenate is clarified at 5000 rpm for 5 minutes in a Sorval HB-4 rotor and the RNA is precipitated by the addition of 0.5 volumes of ethanol. The RNA is dissolved and precipitated 3 more times from 6 M guanidine hydrochloride before being dissolved in $H_2O$.

Messenger RNA from this pool is enriched by chromatography on oligo (dT) cellulose (Collaborative Research).

This mRNA is then subjected to electrophoresis through an agarose gel containing formaldehyde, as described by Maniatis et al., supra, at 202 3. The mRNA in the gel is then transferred to a nitrocellulose filter (Maniatis et al., at 203-4).

The thus obtained mRNA is hybridized with the radiolabeled porcine exon DNA obtained as described above, and the existence of hybrids detected by autoradiography. A radioactive signal indicates that the tissue source of the mRNA is a source of synthesis of AHF in the body.

Alternatively, mRNA can be screened using the $S_1$ protection screening method.

$S_1$ nuclease is an enzyme which hydrolyzes single stranded DNA, but does not hydrolyze base paired nucleotides, such as hybridized mRNA/DNA. Thus the existence of a radioactive band after acrylamide gel electrophoresis and autoradiography shows that the single stranded DNA corresponding to the AHF exon has been protected by the complementary mRNA, i.e. the mRNA for AHF. Thus the tissue which was the source of that mRNA is a site of synthesis of AHF in vivo. That tissue can be used as a source for AHF mRNA. This method of screening can be somewhat more sensitive than screening method described above.

A probe consisting of single stranded radioactively labeled DNA complementary to the mRNA is synthesized using the universal primer of M13 to prime DNA synthesis of the porcine genomic subclone 34-H1. The reaction is performed in a 100 µl solution of 50 mM Tris pH 7.4, 5 mM $MgCl_2$, 1 mM 2-mercaptoethanol, 50 mM NaCl, 40 µM dGTP, dTTP, dCTP, 60 µCi of $^{32}P$-dATP (400Ci/mmole), 10 ng universal primer, 200–400 ng of 34-53 template DNA, and the Klenow fragment of DNA polymerase I (*E. coli*). The reaction is incubated at 23° C. for 60 minutes, 10 minutes at 70° C., 50 units of PstI added and incubated an additional 60 minutes.

The reaction is terminated by phenol/chloroform extraction, NaCl added to 0.2M and then precipitated with two volumes 100% ethanol. The precipitated DNA is pelleted by centrifugation, redissolved in 20% sucrose, 50 mM NaOH, 0.1% cresol green and then electrophoresed through 2% agarose in 50 mM NaOH, 10 mM EDTA. The resultin9 single stranded fragment is localized by autoradiography, the band excised and DNA isolated by electroelution in dialysis tubing.

Sample mRNA is prepared from liver, spleen, etc. tissue by the guanadine hydrochloride method described above.

The probe is then hybridized to sample mRNA (obtained from the oligo (dT) chromatography enriching step) in 50% formamide, 0.4M NaCl, 40 mM PIPES [piperazine-N,N' bis(2-ethanesulfonic acid)]pH 6.5, 1 mM EDTA, 5–50 µg mRNA, 2 ug labeled DNA in a volume of 15 µl. The hybridization is terminated by the addition of 200 µl cold S1 nuclease buffer (0.25 M NaCl, 0.3 M $NaCH_3COO$[pH 4.5], 1 mM $ZnSO_4$, 5% glycerol, and 1000 units $S_1$ nuclease. The reaction is incubated at 45° C. for 30 minutes. Samples are phenol extracted, ethanol precipitated with 10 µg yeast tRNA carrier and subjected to analysis by electrophoresis through 5% polyacrylamide sequencing gels as described in Maxam-Gilbert, *PNAS USA,* 74:560 (1977).

EXAMPLE 6: USE OF AHF EXON DNA TO OBTAIN AHF mRNA FROM TISSUE

Once a tissue which is a source of mRNA is identified, AHF mRNA from that tissue is extracted and used to construct a cDNA library. The cDNA library is then utilized for identifying and constructing a full length cDNA clone which encodes the amino acid sequence for AHF, without the introns contained in the genomic clone, as described below. Thereafter, the cDNA which encodes the AHF protein is inserted into an appropriate expression vector, in an appropriate host, for expression of AHF.

Since human AHF is in great demand for treatment of hemophilia and other uses, the preparation of human AHF cDNA is described.

1. Obtaining mRNA for Human AHF mRNA from the human tissue responsible for AHF synthesis is prepared by guanidine hydrochloride extraction as described by Cox and disclosed above.

Further fractionation of mRNA obtained from the oligo (dT) cellulose chromatography column is obtained by sedimenting on 5-20% sucrose gradients containing 10 mM Tris-HCl (pH 7.4), lmM EDTA and 0.2% SDS by centrifugation for 24 hours at 22,000 rpm in a Beckman SW28 rotor. Fractions (1.0 ml) are collected, sodium acetate was added to 0.2M, and the fractions are ethanol precipitated twice before dissolving in water. The size distribution of the fractionated RNA is determined by electrophoresis through 1.4% agarose gels containing 2.2 M formaldehyde.

mRNA sedimenting with an S (Svedberg) value greater than 28 is pooled for the synthesis of double stranded cDNA. 10 $\mu$g of this RNA is denatured at room temperature in 10 $\mu$l of 10 mM methylmercuryhydroxide. 140 mM 2-mercaptoethanol is added to inactivate the methylmercuryhydroxide. The RNA is then diluted to 50 $\mu$l containing 140 mM KCl, 100 mM Tris-HCl (pH 8.3 at 42° C.), 1 mM of each deoxynucleotide triphosphate, 200 $\mu$g/ml oligo(dT)12-18, 10 mM MgCl$_2$, and 0.1 $\mu$Ci $^{32}$P-dCTP/ml. These reactions are performed at 42° C. for 1 hour after the addition of 3 $\mu$l of 17 units/$\mu$l AMV reverse transcriptase (Life Sciences). The reaction is terminated by the addition of 0.25 M EDTA (pH 8.0) to 20 mM. The resulting mixture is extracted once with an equal volume of phenol/chloroform (1:1) followed by one chloroform extraction. The sample is then chromatographed on a 5 ml Sepharose CL-4B column (Pharmacia) equilibrated in 10 mM Tris-HCl (pH 8.00, 100 mM NaCl, 1 mM EDTA. The void volume is collected and the nucleic acids (including any RNA/cDNA hybrids) are precipitated by the addition of 2.5 volumes of ethanol.

Preferably in conjunction with the above procedures an AHF exon oligonucleotide segment is also used in place of oligo dTr to prime the reverse transcription, as described in Ullrich et al., *Nature*, 303:821 (1983).

The RNA-cDNA hybrids are dissolved in 35 $\mu$l of deionized H$_2$O, made 100 mM potassium cacodylate (pH 6.8), 100 $\mu$M dCTP, 1 mM 2-mercaptoethanol, 1 mM cobalt chloride and enzymatically "tailed" by the addition of 10 units of deoxytidyl terminal transerase (pH Biochemicals) and incubating the reaction for 30 seconds at 37° C. The reaction is terminated by adding 0.25 M EDTA to 10 mM. Tris-HCl (pH 8.0) is added to 300 mM and the sample extracted once with an equal volume of phenol-chloroform (1:1) and then with an equal volume of chloroform. Nucleic acids are precipitated from this product by the addition of 2.5 volumes of ethanol.

The dC tailed hybrid molecules are then annealed with 170 $\mu$g/ml oligo(dG)14-18 cellulose in 10 mM KCl, 1 mM EDTA for 10 minutes at 43° C. and then an additional 10 minutes at 23° C. This reaction product is then diluted to 100 $\mu$l containing 100 mM ammonium sulfate, 1 mM 2-mercaptoethanol, 100 mM MgCl$_2$, 100 $\mu$g/ml bovine serum albumin (Sigma, Cohn fraction V), and 100 $\mu$M nicotinamide adenine dinucleotide. Second strand cDNA synthesis is initiated by the addition of 1 unit RNase H (P-L Biochemicals), 1 unit of *E. coli* DNA ligase, and 10 units of DNA polymerase I and incubated at 16° C. for 12 hours.

The sample is then chromatographed over Sepharose CL-4B as described above. Double stranded DNA is ethanol precipitated and dC tailed as described for the RNA-cDNA hybrid tailing.

2. Screening for Human AHF DNA dC tailed double stranded cDNA obtained as described above is annealed with an equimolar amount of dG tailed pBR322 (New England Nuclear) in 10 mM Tris-HCl (pH 8.0), 1 mM EDTA, 100 mM NaCl at 37° for 2 hours. The annealed chimeric molecules are then frozen at $-20°$ C. until use in bacterial transformation.

Bacterial transformation is done using the MC1061 strain of *E. coli* (source). Cells (50 ml) are grown to an optical density of 0.25 at 600 nm. Cells are concentrated by centrifugation at 2,500 rpm for 12 minutes, washed in 10 ml of sterile 100 mM CaCl$_2$, and again pelleted by centrifugation as described above. Cells are resuspended in 2 ml of sterile 100 mM CaCl$_2$ and kept at 4° for 12 hours. The annealed chimeric molecules are incubated at a ratio of 5 ng of double stranded cDNA per 200 $\mu$l competent cells at 4° C. for 30 minutes. The bacteria are then subjected to a two minute heat pulse of 42° C. 1.0 ml of L-broth is then added and the cells incubated for 1 hour at 37°. Cells are then plated onto LB-agar plates containing 5 $\mu$g/ml tetracycline.

Human AHF clones are identified using the colony hybridization procedure of Grunstein and Hogness *PNAS U.S.A.* 72:3961 (1975), the disclosure of which is incorporated herein by reference. The cDNA library is plated onto a nitrocellulose filter (Schleicher and Schuell) overlaying L-broth/ 5 $\mu$g/ml tetracycline agar plates. Colonies are grown overnight at 37° C. and then the filter placed on sterile Whatman 3 M paper. A premoistened nitrocellulose filter is then pressed against the master filter and the filters keyed using an 18 gauge needle. The replica filter is then grown on LB-tetracycline plates at 37° C. until the colonies reached a diameter of 1-2 mm. The filters are then transferred to LB plates containing 150 $\mu$g/ml chloramphenicol and incubated at 37° C. for 16-24 hours.

Filters are then removed and placed onto Whatman 3 M paper saturated with 0.5 M NaOH for 5 minutes at room temperature. Filters are then neutralized by placing onto Whatman 3 M saturated with 1 M Tris-HCl (pH 7.5), 1.5 M NaCl, and then Whatman 3 M saturated with 2x standard saline citrate (SSC). SSC (lx) is 0.15 M NaCl, 0.015 M sodium citrate.

Filters are air dried and baked in vacuo at 80° C. for 2 hours. Prehybridization of filters is done at 65° C. for 30 minutes in 10 mM Tris-HCl (pH 8.0), 1 mM EDTA, 0.1% SDS followed by 30 minutes in 7x SSC, 5x Denhardt's (lx Denhardt's is 0.02% polyvinylpyrollidine, 0.02% ficoll, 0.02% bovine serum albumin), 100 $\mu$g/ml denatured salmon sperm DNA, and 0.1% SDS. $^{32}$P-labelled human exon DNA, prepared as described above, are added to $10^6$ cpm/ml and the hybridization performed 12-16 hours at 37° C. Filters are then washed in several changes of 7x SSC, 0.1% SDS for 1-2 hours at 37° C. Filters are then air-dried and subjected to autoradiography with Kodak XAR film and a Dupont Lightning Plus intensifying screen.

Those colonies showing a hybridization signal above background are grown in L-broth containing 50 μg/ml tetracycline for rapid prep purification of plasmid DNA. Plasmid DNA is purified by the method of Holmes et al., *Anal. Biochem.*, 114:193 (1981), the disclosure of which is incorporated herein by reference. An aliquot of this DNA is cleaved with restriction endonuclease Pst 1 and the fragments electrophoresed through 1% agarose/TBE gels and blotted according to the procedure of E. Southern, *J. Mol. Biol.* 98:503 (1975), *Methods Enzymol.* 69:152 (1980), the disclosure of which is incorporated herein by reference. The nitrocellulose filters are hybridized with radiolabeled human AHF exon DNA as described for colony hybridization. Those plasmids which contained Pst I inserts hybridizing to the AHF exon DNA are used for DNA sequencing analysis.

For sequencing, plasmid DNA, (purified from 0.75 ml of culture by the procedure of Holmes, et al., supra), is digested to completion with the restriction endonuclease Sau 3aI. The resulting DNA segment, identified as 34-S1, has a DNA sequence which is depicted in FIG. 4. The DNA is ethanol precipitated after extraction with phenol-chloroform and redissolved in 10 μl TE (10 mM Tris-HCl pH 8.0, 1 mM EDTA). 5 μl of the DNA solution is ligated with 20 ng of Bam Hl cleaved M13 mp 9 replicative form DNA in 100 μl of 50 mM Tris-HCl (pH 7.4), 10 mM MgCl$_2$, 10 mM dithiothreitol, 1 mM ATP and an excess of T4 DNA ligase. Ligations are done at 15° C. for 2-4 hours.

5 μl of the ligation reactions are used to transform 200 μl of *E. coli* strain JM101/TG1 as described above. Recombinants are identified as white plaques when grown on LB-agar plates containing X-gal as an indication for beta-galactosidase activity as described by Davies, et al., *J. Mol. Biol.* 36:413 (1968).

Recombinant pha9e harboring sequences hybridizing to the human exon are identified by the procedure of Benton, et al., *Science* 196:180 (1977), the disclosure of which is incorporated herein by reference, using radioactively labelled human AHF exon as a probe. Plaques showing a hybridization signal are picked and grown in 1.5 ml cultures of L-broth. Single-stranded phage DNA prepared from these cultures is used as template in oligonucleotide-primed DNA synthesis reactions. Sequencing is done using the dideoxy chain-termination procedure, see, e.g., Sanger et al., *PNAS U.S.A.* 74:5463 (1977).

Human AHF recombinants are identified by comparing their nucleotide sequence with that which is known from the human exon sequence of human AHF.

3. Porcine AHF mRNA

Human AHF recombinants are used to screen a porcine tissue library constructed exactly as described for the human tissue cDNA library. Prospective porcine AHF recombinant DNA clones are identified by the Grunstein-Hogness procedure using the porcine $^{32}$p labeled exon fragment as a probe as described above. The probe is the porcine AHF exon segment labelled with 32P by nick-translation as described by Rigby et al., *J. Mol. Biol.*, 113:237 (1977), the disclosure of which is incorporated herein by reference.

Colonies exhibiting hybridization signals are grown for rapid prep plasmid purification purposes as described above. Plasmid DNA is cleaved with the restriction endonuclease Pst 1, electrophoresed through 1% agarose/TBE gels, and blotted according to the procedure of E. Southern (1975). The blots are hybridized with nick-translated porcine AHF recombinant DNA labelled with $^{32}$P.

Full-length clones may be constructed in a conventional manner, such as by ligation of DNA fragments from overlapping clones at restriction enzyme sites common to both clones as is well known in the art ("gene walking").

4. Identifying Full-length Clones from Steps 2 or 3

The distance between the 5' end of an existing clone and the 5' end of the mRNA can be analyzed by the primer-extension technique described in A9arwal et al., "J.B.C." 256(2):1023-1028 (1981) utilizing an oligonucleotide primer whose sequence comes from the 5' (amino-terminal) region of the existing AHF clone. If gels developed using this procedure show more than one transcript one should consider the most intense band as representing the full mRNA transcript.

There are, however, many mRNAs which contain a long region of 5' untranslated sequence. Thus, expression of human AHN DNA may not be contingent upon the acquisition of a complete cDNA clone. For example, a clone may be obtained which by DNA sequencing analysis demonstrates the existence of a methionine codon followed by a sequence which is analogous to or identical to a known eucaryotic protein secretion signal and which is in frame with the remaining codons. Transformation and expression should be conducted for a clone which contains the met-secretion signal sequence, which is of the expected size and which contains a poly (T) 3' terminus.

EXAMPLE 7

Expression of Human or Porcine AHF

This example contemplates expression of AHF using the full length clone obtained by the method of Example 6 in a cotransformation system.

(a) Preparation of Transformation Vector

A direct method for obtaining the AHF transformation vector is described below. The pCVSVL plasmid is partially digested with Pst I, the digest separated on gel electrophoresis. After visualization, the linear DNA fragment band corresponding to full length plasmid is isolated as plasmid pCVSVL-B1.

The cDNA for AHF is rescued from the Example 5 cloning vectors by partial digest with Pst I. The partial digest is separated on gel electrophoresis, and the band corresponding to the molecular weight of the full length cDNA is isolated. pCVSVL-B1 is annealed with this plasmid, ligated with T4 ligase at 15° C., transfected into *E. coli* strain HB101 and transformants selected for tetracycline resistance. The selected *E. coli* transformants are grown in the presence of tetracycline. Plasmid pCVSVL-B1a is recovered in conventional fashion from this fermentation. Proper orientation of the cDNA in the plasmid may be determined in conventional fashion by assymetric digestion with endo nuclease.

(b) Cotransformation; Selection and Amplification

Plasmid pCVSVL-A1a or pCVSVL-B1a and pAdD26SVpA#3 (Kaufman et al., op. cit.) are mixed together (50 μg HP and 0.5 μg pAdD265VpA #3) and precipitated by the addition of NaOAc pH 4.5 to 0.3M and 2.5 vols. of ethanol. Precipitated DNA is allowed to air dry, is resuspended in 2X HEBSS (5.0 ml) and mixed vigorously with 0.25 M CaCl$_2$ (5 ml) as described (Kaufman et al., op. cit). The calcium-phosphate-DNA precipitate is allowed to sit 30' at room temperature and applied to CHO DUKX-B1 cells (Chasin and Urlaub, 1980, available from Columbia University). The growth an maintenance of these cells has been described (Kaufman et al., op. cit, Chasin and Urlaub 1980).

The DUKX-B1 cells are subcultured at $5 \times 10^5$/10cm dish 24 hr. prior to transfection. After 30 minutes incubation at room temperature, 5 ml of a media with 10% fetal calf serum is applied and the cells are incubated at 37° for 4.5 hr. The media is then removed from the monolayer, 2 ml of a-media with 10% fetal calf serum, 10μg/ml of thymidine, adenosine, and deoxyadenosine, and penicillin and streptomycin. Two days later the cells are subcultured 1:15 into a-media with 10% dialyzed fetal calf serum, and penicillin and streptomycin, but lacking nucleosides. Cells are then fed again with the same media after 4–5 days.

Colonies appear 10-12 days after subculturing into selective media. Methotrexate (MTX) selection and detection of AHF gene and selection gene amplification are conducted in accordance with Axel et a., U.S. Pat. No. 4,399,216, or Kaufman et al., op. cit.

AHF yields are improved by cotransforming the permanent cell line EA.hy 926 (Edgell et al., "Proc. Natl. Acad. Sci" 80:3734-3737 (1983) in place of DUKX-B1 cells. In this case the cotransforming selection gene should be the dominant DHFR gene disclosed by Haber et al., "Somatic Cell Genetics" 4:499–508 (1982). Otherwise, the cotransformation and culture will be substantially as set forth elsewhere herein.

(c) Production of AHF

AHF-producing CHO transformants selected in part (e) are maintained in seed culture using standard techniques. The culture has scaled up to 10 liters by cell culture in conventional media. This medium need not contain MTX and will not contain nucleosides so as to exclude selection gene revertants.

The fermentation supernatant is monitored for clotting activity following standard assays for use with blood plasma samples (reduction in clotting time of Factor VIII-deficient plasma). The supernatant may be purified by conventional techniques such as polyethylene glycol and glycine precipitations (as are known for use in purifying AHF from blood plasma) in order to increase the sensitivity of the FACTOR VIII assays.

When FACTOR VIII clotting activity has reached a peak the cells are separated from the culture medium by centrifugation. The Factor VIII is then recovered and purified by polyethylene glycol and glycine precipitations. Clotting activity was demonstrated in Factor VIII deficient plasma.

I claim:

1. An isolated recombinant vector containing DNA coding for human factor VIII:C, comprising a polydeoxyribonucleotide having the sequence:

5' CGC AGC TTT CAG AAG AAA ACA CGA CAC
      TAT TTT ATT GCT GCA GTG GAG AGG 3'

2. The recombinant vector DNA of claim 1, wherein said DNA is human genomic DNA.

3. The vector of claim 1, wherein the DNA coding for human factor VIII:C is linked directly or indirectly to DNA from a non-human source.

4. A non-human recombinant expression vector for human factor VIII:C comprising a DNA segment having the sequence:

5' CGC AGC TTT CAG AAG AAA ACA CGA CAC
      TAT TTT ATT GCT GCA GTG GAG AGG 3' operatively linked to a heterologous regulatory control sequence.

5. A transformed non-human mammalian cell line containing the expression vector of claim 4.

6. A screening agent for identifying deoxyribonucleotide sequences and ribonucleotide sequences which encode for at least a portion of the human gene factor VIII:C, consisting essentially of a deoxyribonucleotide having the following sequence or its inverse complement:

5'TTT CAG AAG AGA ACC CGA CAC TAT TTC
     ATT GCT GCG GTG GAG CAG CTC TGG GAT
     TAC GGC ATG AGC GAA TCC CCC CGG GCG
     CTA AGA AAC AGG 3'.

7. A method of producing a protein having factor VIII:c procoagulant activity, comprising the steps of:
   (1) culturing an isolated cell transformed with double stranded DNA which DNA
      (a) has been operatively linked to a heterologous regulatory control sequence,
      (b) hybridizes under stringent conditions to the following nucleotide sequence:

5' GAC ATT TAT GAT GAG GAT GAA
         ATT CAG ACG CCC CGC AGC TTT
         CAG AAG AAA ACA CGA CAC TAT
         TTT ATT GCT GCA GTG GAG AGG and
      (c) encodes a protein which upon expression exhibits human factor VIII:c procoagulant activity, and
   (2) recovering said protein from the culture.

8. A transformed non-human mammalian cell containing a gene encoding human factor VIII:c in operable association with a heterlogous regulatory control sequence in an expression vector therefor.

* * * * *

UNITED STATES PATENT AND TRADEMARK OFFICE

CERTIFICATE EXTENDING PATENT TERM
UNDER 35 U.S.C. § 156

PATENT NO.: 4,757,006

DATED: July 12, 1988

INVENTORS: John J. Toole, Jr. et al.

PATENT OWNER: Genetics Institute, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

516 DAYS with all rights pertaining thereto as provided by 35 U.S.C. § 156(b).

I have caused the seal of the Patent and Trademark Office to be affixed this 20th day of September 1994.

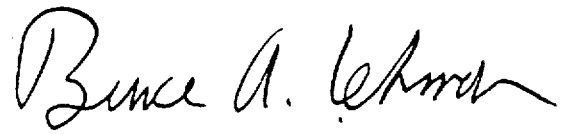

Bruce A. Lehman
Assistant Secretary of Commerce and
Commissioner of Patents and Trademarks